United States Patent [19]

Gilbert et al.

[11] Patent Number: 5,324,734
[45] Date of Patent: Jun. 28, 1994

[54] OXIDIZATION METABOLITES OF 5-α-23-METHYL-4-AZA-21-NOR-CHOL-1-ENE-3, 20-DIONE

[75] Inventors: John D. Gilbert, Ambler, Pa.; Timothy V. Olah, Collingswood, N.J.

[73] Assignee: Merck & Co., Inc., Rahway, N.J.

[21] Appl. No.: 945,204

[22] Filed: Sep. 15, 1992

[51] Int. Cl.$^5$ .................. C07D 221/02; A61K 31/47
[52] U.S. Cl. ..................................... 514/281; 546/77
[58] Field of Search ..................... 514/284; 546/77

[56] References Cited

U.S. PATENT DOCUMENTS

| | | | |
|---|---|---|---|
| 2,227,876 | 1/1940 | Bolt | 546/77 |
| 3,239,417 | 3/1966 | DiTullio et al. | 546/77 |
| 3,264,301 | 8/1966 | Doorenbos et al. | 546/77 |
| 3,285,918 | 11/1966 | Doorenbos et al. | |
| 4,220,775 | 2/1980 | Rasmusson et al. | 546/77 |
| 4,317,817 | 3/1982 | Blohm et al. | |
| 4,377,584 | 3/1983 | Rasmusson et al. | 546/77 |
| 4,732,897 | 3/1988 | Cainelli et al. | 546/77 |
| 4,760,071 | 7/1988 | Rasmusson et al. | 546/77 |
| 4,845,104 | 7/1989 | Carlin et al. | 546/77 |
| 4,859,681 | 8/1989 | Rasmusson et al. | 546/77 |
| 4,882,319 | 11/1989 | Holt et al. | 546/77 |
| 4,888,336 | 12/1989 | Holt et al. | 546/77 |
| 4,910,226 | 3/1990 | Holt et al. | 546/195 |
| 5,098,908 | 3/1992 | Steinberg et al. | 546/77 |
| 5,120,742 | 6/1992 | Rasmusson | 514/284 |
| 5,175,155 | 12/1992 | Juniewicz et al. | 514/284 |

FOREIGN PATENT DOCUMENTS

| | | |
|---|---|---|
| 970692 | 7/1975 | Canada . |
| 004949 | 10/1979 | European Pat. Off. . |
| 115096 | 9/1985 | European Pat. Off. . |
| 277002 | 8/1988 | European Pat. Off. . |
| 289327 | 11/1988 | European Pat. Off. . |
| 314199 | 5/1989 | European Pat. Off. . |
| 343954 | 11/1989 | European Pat. Off. . |
| 375344 | 6/1990 | European Pat. Off. . |
| 375345 | 6/1990 | European Pat. Off. . |
| 375347 | 6/1990 | European Pat. Off. . |
| 375349 | 6/1990 | European Pat. Off. . |
| 1465544 | 11/1965 | France . |

OTHER PUBLICATIONS

J. Carlin et al. Drug Metabolism & Disposition, vol. 20, pp. 148-155 (1992).
J. Gilbert et al. Biolog. Mass. Spectromety, vol. 21, pp. 341-346 (1992).
Diani et al, Jour. of Clin & Metab vol. 74 pp. 345-350 (1992).
Stinson, Chem. Eng. News Jun 29, 1992, pp. 7-8.
Helliker, Wall St. Journ. 7 Jun. 1991, pp. A1, A7 (1991).
Gilbert Chem. Abstr. vol. 117 Entry 82802j (1992).
Neri, et al., Endo, vol. 91, No. 2 (1972), pp. 427-437.
Nayfeh et al., Steroids, 14, 269 (1969).

(List continued on next page.)

*Primary Examiner*—Donald G. Daus
*Attorney, Agent, or Firm*—C. M. Caruso; R. J. North; C. S. Quagliato

[57] ABSTRACT

The compounds of formula (I)

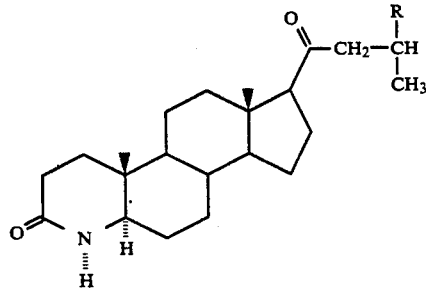

wherein R is selected from the group hydroxymethyl and carboxy, have been identified as metabolites of 5α-23-methyl-4-aza-21-nor-chol-1-ene-3,20-dione and are believed to be active as testosterone 5α-reductase inhibitors and would thus be useful for treatment of acne, seborrhea, female hirsutism or benign prostatic hypertrophy.

3 Claims, 3 Drawing Sheets

OTHER PUBLICATIONS

Doorenbos and Solomons, J. Pharm., Sci., 60, 8, (1973), pp. 638–640.
Doorenbos and Brown, J. Pharm. Sci., 60, 8, (1971), pp. 1234–1235.
Doorenbos and Kim, J. Pharm. Sci., 63, 4, (1974) pp. 620–622.
Rosmusson et al., J. Med. Chem., 29 (11) (1986), pp. 2298–2315.
Brooks et al., Prostate, (1) (1986), pp. 65–75.
Brooks et al. Steroids, 47 (1) (1986), pp. 1–19.
Liang et al., Endocr., 117 (2) (1985) pp. 1–19.
Rasmusson et al., J. Med. Chem., 27 (12) (1984) pp. 1690–1701.
Back, J. Org. Chem., vol. 46, No. 7 (1981) pp. 1442–1446.
Liang et al., Chem. Abstracts, vol. 95, 109055j (1981).
Kadahoma et al., JNCI, vol. 74, No. 2 (Feb. 1985) pp. 475–481.
Andriole et al., The Prostate, vol. 10, (1987) pp. 189–197.
Bingham et al. J. Endocr., vol. 57 (1973) pp. 111–121.
Kedderis, Toxicol. Appl. Pharmacol., vol. 103, (1990) pp. 222–227.
Metcalf et al., Bioorganic Chemistry, 17, (1986) pp. 372–376.
Levy et al., Biochemistry, vol. 29 (1990) pp. 2815–2824.
Holt et al., J. Med. Chem. vol. 33 (1990) pp. 943–950.
Levy et al., J. Steroid Biochem., vol. 34, Nos. 1–6 (1989) pp. 571–575.
Holt et al., J. Med. Chem., vol. 33 (1990) pp. 937–942.
Metcalf et al., TIPS, vol. 10 (Dec. 1989) pp. 491–495.
Murphy et al., Steroids, vol. 35, No. 3 (Mar. 1980) 1–7.
Stone et al., Prostate. vol. 9 (1986) pp. 311–318.
Brooks et al., Steroids, vol. 47 No. 1 (1986) pp. 1–19.
Labrie et al., Lancet, No. 8515, No. 1986 pp. 1095–1096.
Rittmaster et al., J. Clin. Endocrin. and Metabl., vol. 55, No. 1 (1987) pp. 188–193.

5,324,734

OXIDIZATION METABOLITES OF 5-α-23-METHYL-4-AZA-21-NOR-CHOL-1-ENE-3,20-DIONE

BACKGROUND OF THE INVENTION

The present invention is concerned with novel oxidation metabolites of 5α-23-methyl-4-aza-21-nor-chol-1-ene-3,20-dione and the use of such compounds as testosterone-5α-reductase inhibitors.

It is well known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'trifluoromethylisobutyranilide. See Neri et al., Endo., Vol. 91, No. 2(1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lesson symptoms of hyperandrogenic stimulation. Nayfeh et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotesterone caused enlargement of the female hamster flank organ, an androgen dependent sebaceous structure. However, concommitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known in the art as 5α-reductase inhibitors. For example, See U.S. Pat. Nos. 2,227,876, 3,239,417, 3,264,301 and 3,285,918; French Patent No. 1,465,544; Doorenbos and Solomons, J. Pharm, Sci. 62, 4, pp. 638–640 (1973); Doorenbos and Brown, J. Pharm. Sci., 60, 8, pp. 1234–1235 (1971; and Doorenbos and Kim, J. Pharm. Sci. 63, 4, pp. 620–622 (1974).

In addition, U.S. Pat. Nos. 4,377,584, 4,220,775, 4,859,681, 4,760,071 and the articles J. Med. Chem. 27, p. 1690–1701 (1984) and J. Med. Chem. 29,2009–2315 (1986) of Rasmusson, et al., 4,732,897 to Cainelli, et al. describe 4-aza-17β-substituted-5α-androstant-3-ones which are said to be useful in the treatment of DHT-related hyperandrogenic conditions.

The compounds of the present invention are metabolites resulting from in vivo administration of 5α-23-methyl-4aza-21-nor-chol-1-ene-3,20-dione and are thus believed to be testosterone-5α-reductase inhibitors and thus useful for the treatment of benign prostatic hyperthrophy, acne vulgaris, seborrhea and female hirstism.

DESCRIPTION OF THE INVENTION

Figure 1B:
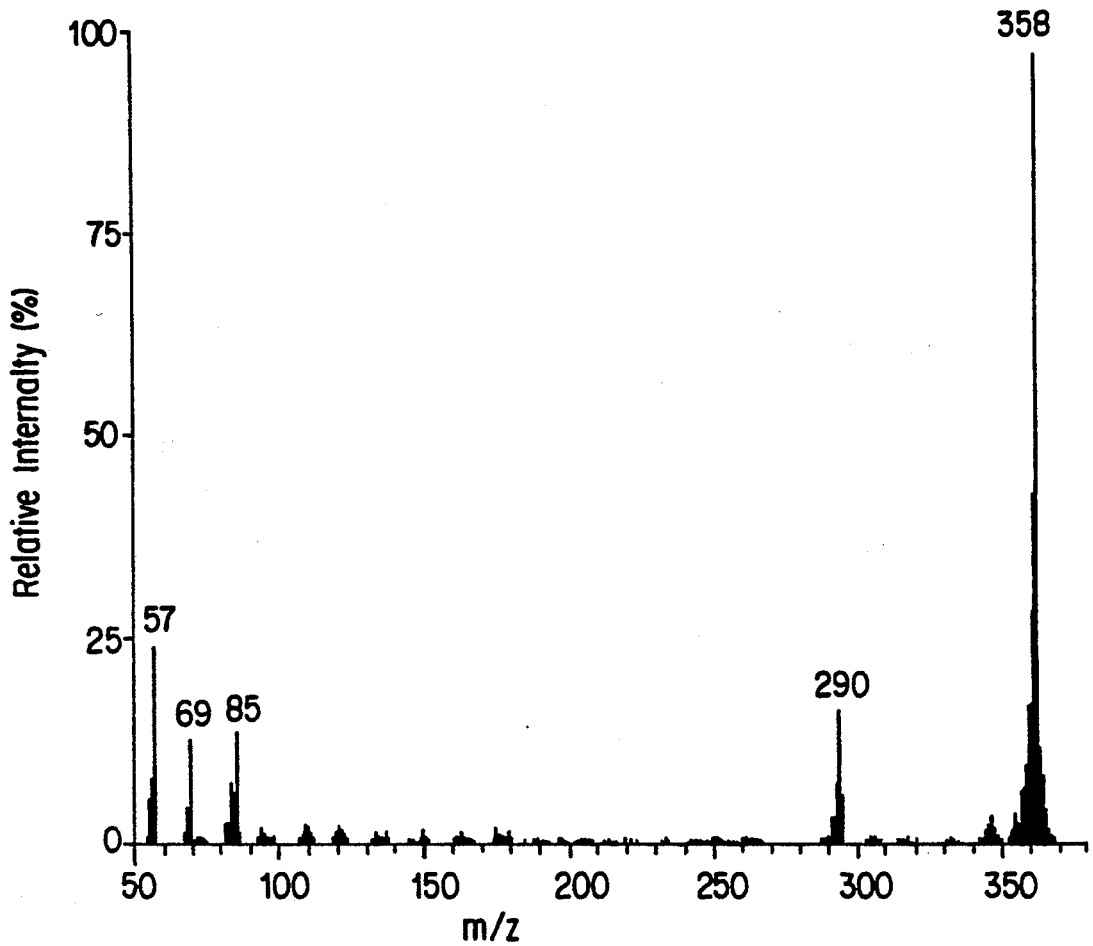
FIG. 1B shows the mass spectrum of the structure in FIG. 1A.

The present invention is concerned with novel oxidation metabolites of 5α-23-methyl-4-aza-21-nor-chol-1-ene-3,20-dione compounds, pharmaceutical formulations comprising the novel compounds as active ingredients and methods of inhibiting testosterone-5α-reductase and of treating hyperandrogenic conditions with the novel compounds of their pharmaceutical formulations.

The present invention is concerned with compounds of the formula

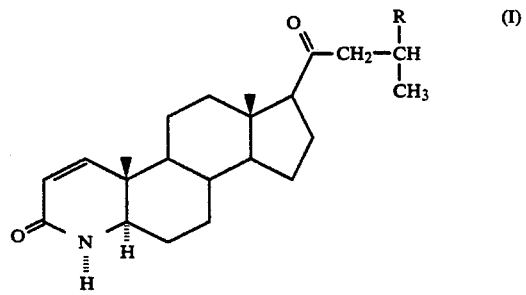

wherein R is selected from the group hydroxymethyl and carboxy; or the pharmaceutically acceptable salts thereof.

These compounds are the oxidative metabolites of 5α-23-methyl-4-aza-21-nor-chol-1-ene-3,20-dione.

Compounds of the present invention include the following:

5α-23-hydroxymethyl-4-aza-21-nor-chol-1-ene-3,20-dione;

5α-23-carboxy-4-aza-21-nor-chol-1-ene-3,20-dione;

The novel compounds of formula I are believed to be oxidative metabolites of 5α-methyl-4-aza-21-nor-chol-1-ene-3,20-dione via the following metabolic sequence.

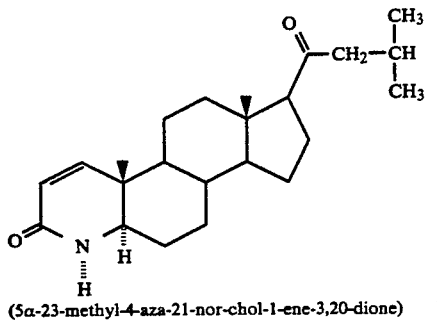

(5α-23-methyl-4-aza-21-nor-chol-1-ene-3,20-dione)

↓ Metabolic Transformation

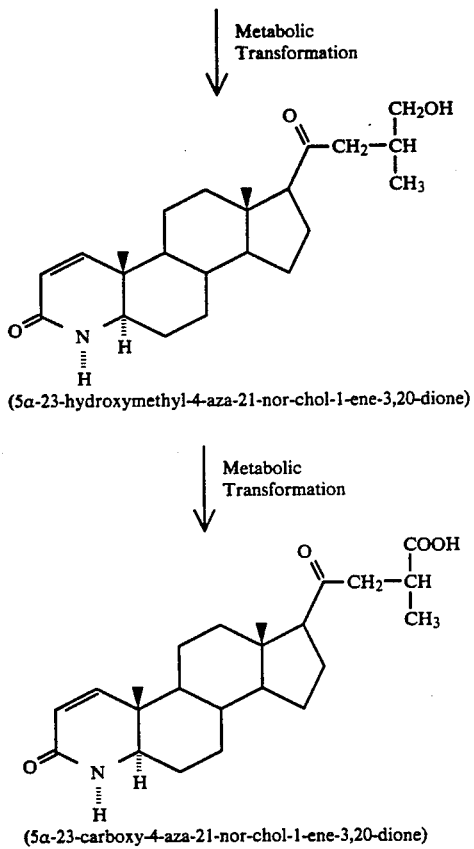

(5α-23-hydroxymethyl-4-aza-21-nor-chol-1-ene-3,20-dione)

↓ Metabolic Transformation (5α-23-carboxy-4-aza-21-nor-chol-1-ene-3,20-dione)

Accordingly, the present invention is particularly concerned with providing a method of treating the hyperandrogenic conditions of acne vulgaris, male pattern baldness, seborrhea and female hirsutism, as well as benign prostatic hypertrophy, by systemic or topical administration of the novel compounds of the present invention.

The present invention is also concerned with providing suitable topical and systemic pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of products may be varied over a wide range varying from 0.5 to 100 mg. per adult human/per day. The compositions are preferably provided in the form of tablets containing 0.5, 1.0, 2.5, 5.0, 10.0, 15.0, 25.0 and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservative are employed when intravenous administration is desired.

For topical administration, the pharmaceutical composition comprises the active compound in combination with a pharmacologically acceptable carrier adapted for topical administration. These topical pharmaceutical compositions may be in the form of a cream, ointment, gel or aerosol formulation adapted for, application to the skin.

The compounds of the present invention were identified as metabolites of 5α-23-methyl-4-aza-21-nor-chol-1-ene-3,20-dione through the following technique.

EXAMPLE I

Four subjects received 25 mgs of 5α-23-methyl-4-aza-21-nor-chol-1-ene-3,20-dione daily for ten days. Plasma was collected 4, 8, 12 and 16 hours post dose on day 10 of the administration. Samples were obtained by pooling C18-solid phase extracts of the plasma. The combined extracts were reduced to dryness and reconstituted in 100 μl of methanol. Twenty μl aliquots were taken for analysis by liquid chromatography/mass spectroscopy/mass spectroscopy (LC/MS/MS). LC/MS/MS was performed on a Sciex API III triple quadruple mass spectrometer interfaced via the heated nebulizer interface to a liquid chromatograph consisting of a Perkin Elmer Series 250 pump, an ISS-100 autoinjector and a 5 cm×4.6 mm, C18, 5 micron Synchrom column. The mobile phase was methanol/0.1% trifluoroacetic acid: 0.010M ammonium acetate/0.1% trifluoroacetic acid (85:15 v/v) at 1 ml/min. The mass spectrometer was operated in the positive ionization mode.

Figure 1A:
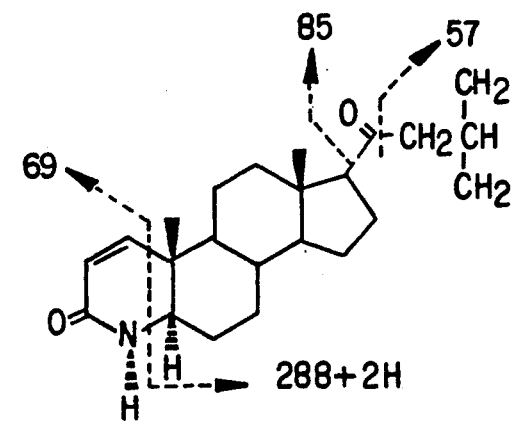
FIG. 1A shows the structural formula of 5α-23-methyl-4-aza-21-nor-chol-1-ene-3,20-dione.
Figure 2B:
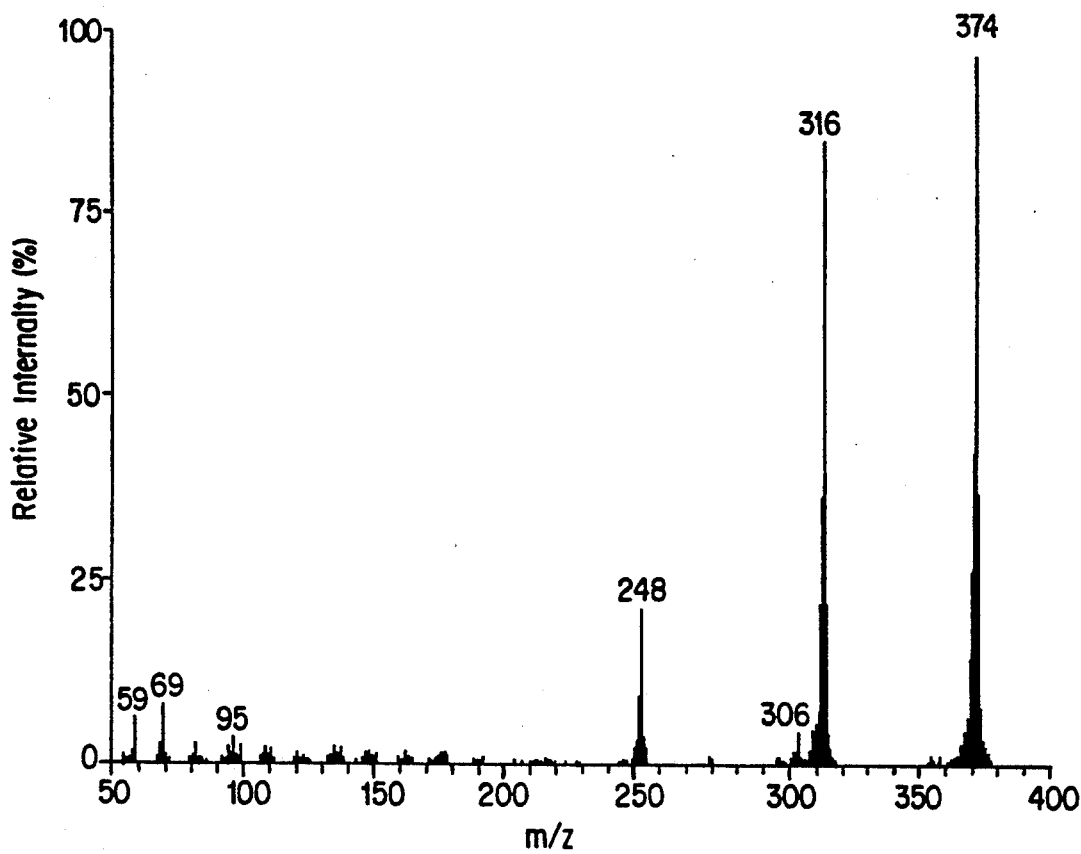
FIG. 2B shows the mass spectrum of metabolite 1.
Figure 2A:
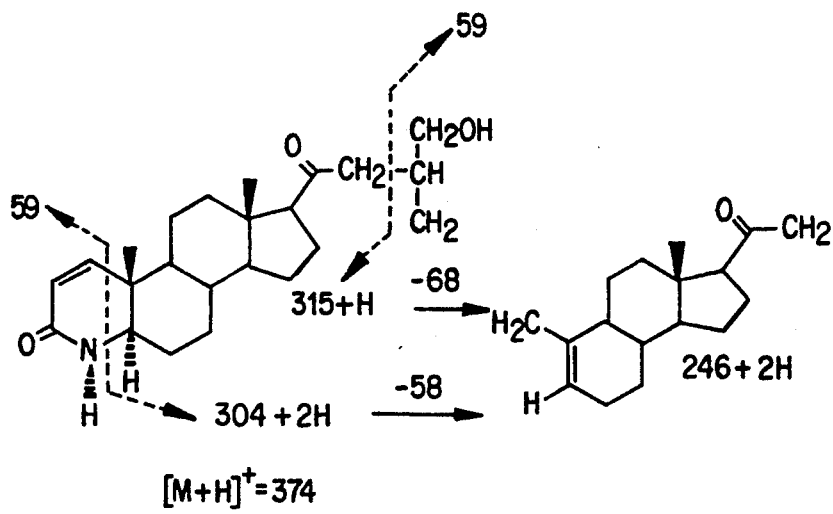
FIG. 2A shows the structural formula of metabolite 1, and a decomposition product thereof.

The daughter ion mass spectrum of 5α-23-methyl-4-aza-21-nor-chol-1-ene-3,20-dione, FIG. 1, indicates diagnostic fragments at m/z 290, 85, 69. The mass spectrum of metabolite 1 is shown in FIG. 2. The spectrum is consistent with hydroxylation of a methyl function on the isobutyl sidechain.

Figure 3B:
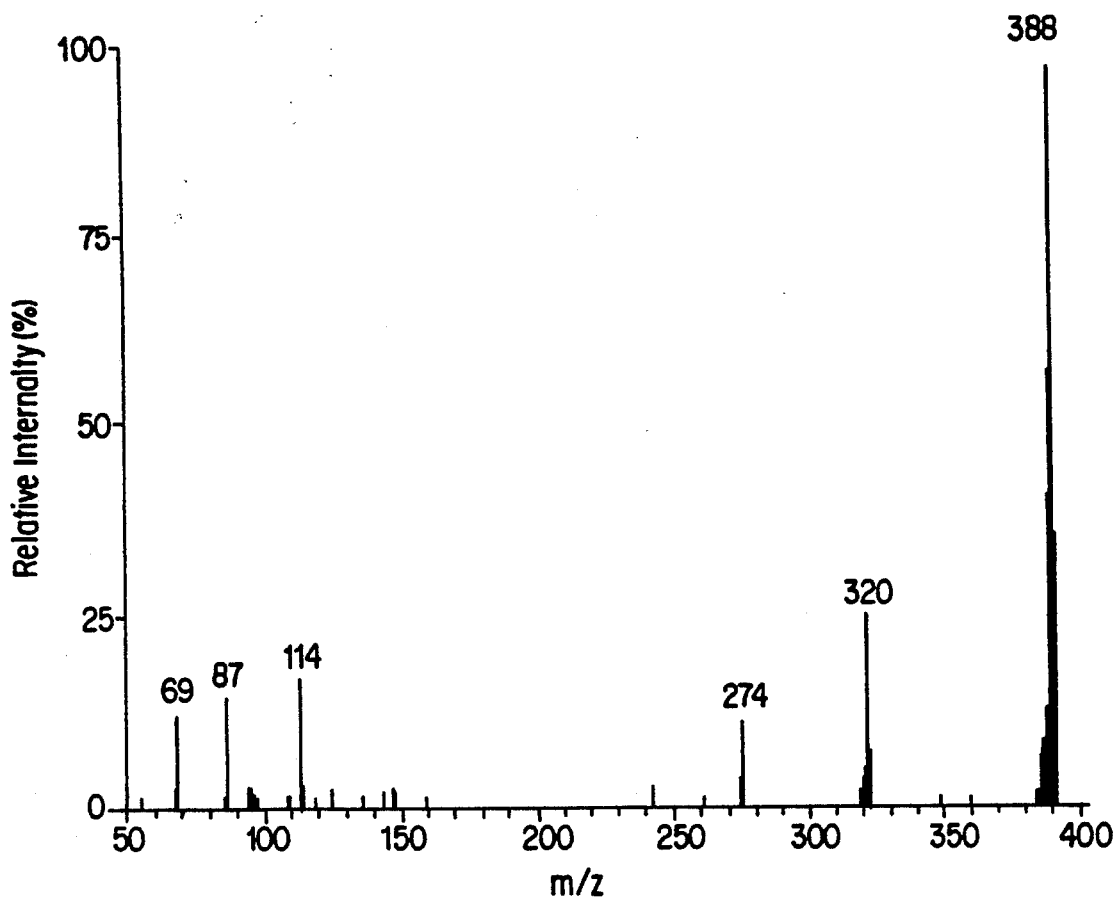
FIG. 3B shows the mass spectrum of metabolite 2.
Figure 3A:
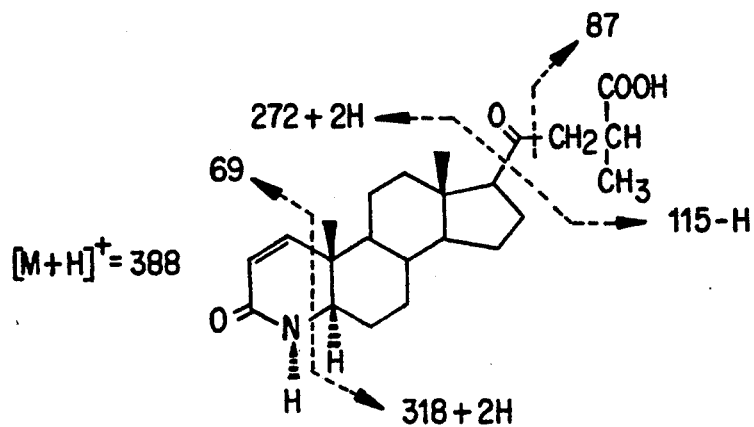
FIG. 3A shows the structural formula of metabolite 2.

The mass spectrum of metabolite 2 is shown in FIG. 3. This spectrum is consistent with oxidation of a methyl group to a carboxylic acid.

What is claimed is:

1. A substantially pure compound of the formula

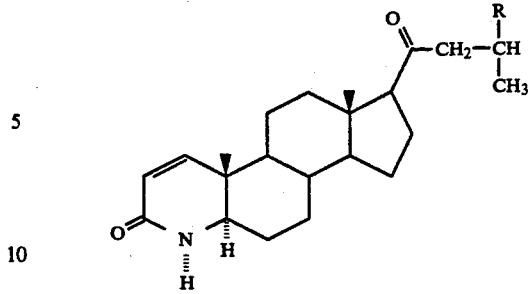
wherein R is hydroxymethyl or carboxy; or the pharmaceutically acceptable salts thereof.
2. A compound of claim 1 which is 5α-23-hydroxymethyl-4-aza-21-nor-chol-1-ene-3,20-dione; 5α-23-carboxy-4-aza-21-nor-chol-1-ene-3,20-dione.
3. A pharmaceutical composition comprising a pharmaceutically acceptable carrier and an antihyperandrogenically effective amount of a compound of claim 1.
* * * * *